United States Patent [19]

Watson

[11] Patent Number: 5,387,188

[45] Date of Patent: Feb. 7, 1995

[54] PULSATILE FLOW-ACCOMMODATING FLUID SHUNT

[75] Inventor: David A. Watson, Goleta, Calif.

[73] Assignee: Pudenz-Schulte Medical Research Corporation, Goleta, Calif.

[21] Appl. No.: 59,897

[22] Filed: May 10, 1993

[51] Int. Cl.[6] .............................................. A61M 5/00
[52] U.S. Cl. ........................................ 604/8; 604/10; 604/247
[58] Field of Search ...................................... 604/8–10, 604/93, 185, 247

[56] References Cited

U.S. PATENT DOCUMENTS

| 3,601,128 | 8/1971 | Hakim ...................................... 604/9 |
| 4,560,375 | 12/1985 | Schulte et al. . |
| 4,795,437 | 1/1989 | Schulte et al. . |
| 4,861,331 | 8/1989 | East et al. . |
| 5,154,693 | 10/1992 | East et al. . |
| 5,176,627 | 1/1993 | Watson . |

Primary Examiner—Randall L. Green
Assistant Examiner—Rob Clarke
Attorney, Agent, or Firm—Kelly, Bauersfeld & Lowry

[57] ABSTRACT

In a cerebrospinal fluid shunt including a flow control device forming a portion of a fluid conduit, a capacitive element is provided for reducing overdrainage of cerebrospinal fluid due to the pulsatile nature of cerebrospinal fluid flow. The capacitive element includes a reservoir having a base and a housing for the base which cooperatively define a fluid flow pathway through the reservoir. A pair of spaced, substantially parallel, flexible diaphragms form opposite sides of the housing such that each flexible diaphragm has an outer surface which forms an exterior surface of the reservoir, and an inner surface in contact with and subject to pressure variations of cerebrospinal fluid within the reservoir. A raised ring surrounds each diaphragm and forms a recess in which the respective diaphragm is positioned. The capacitive element accommodates the pulsatile nature of cerebrospinal fluid flow between a cerebrospinal fluid source and the flow control valve by varying the fluid capacity of the reservoir.

15 Claims, 3 Drawing Sheets

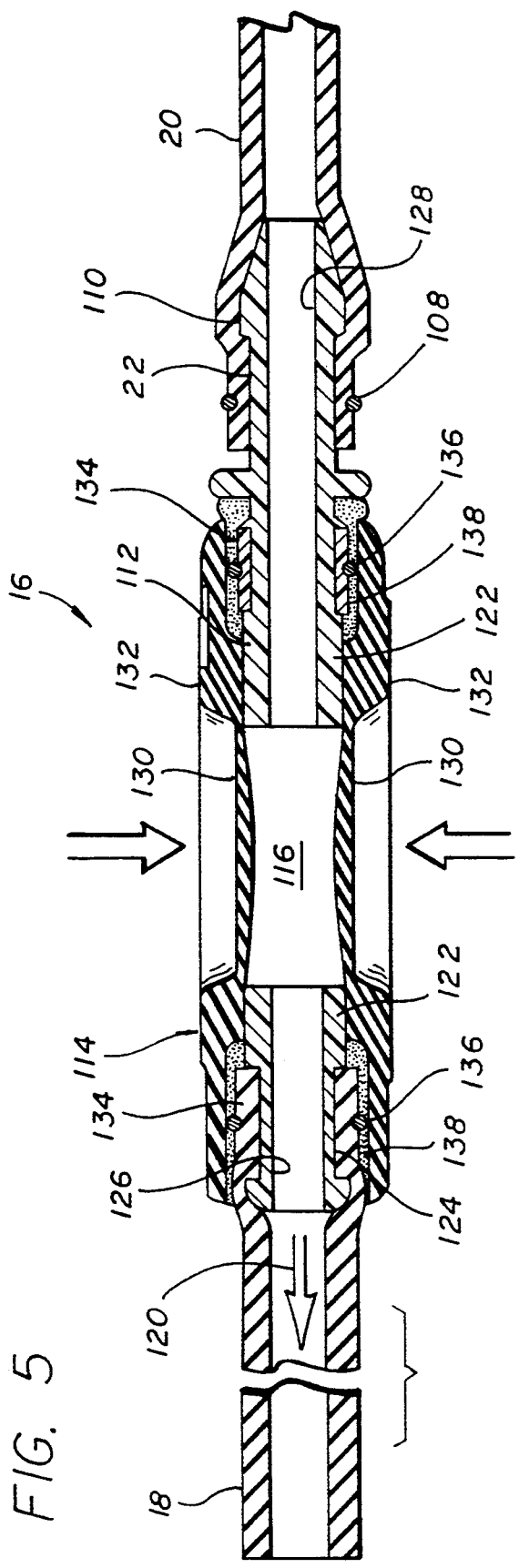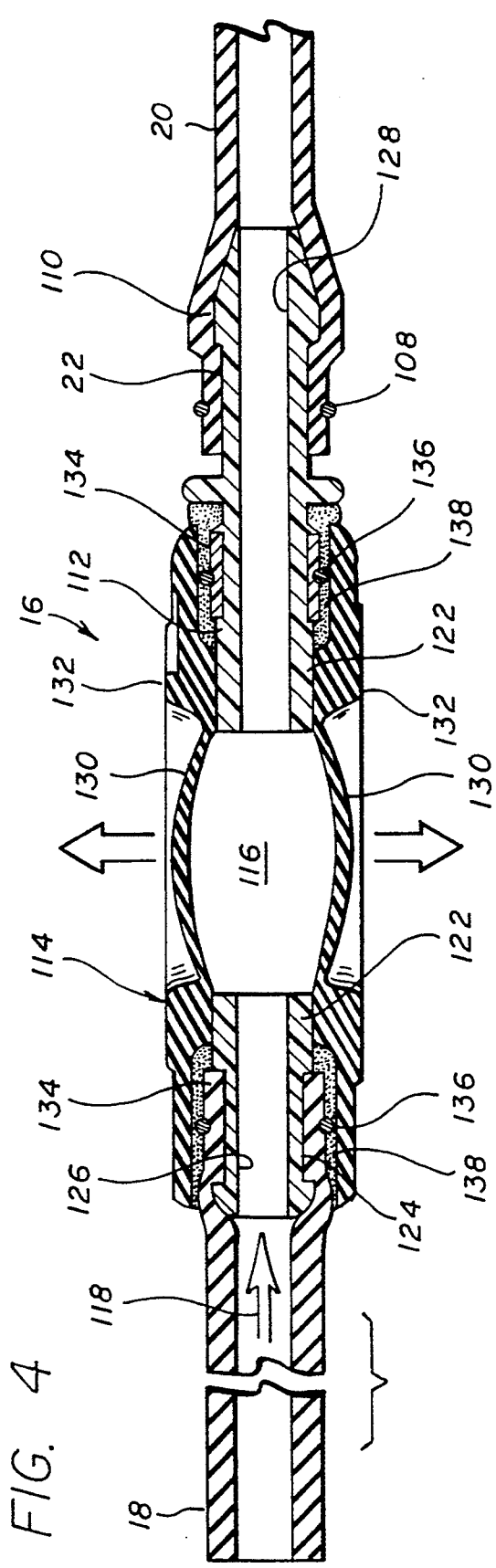

PULSATILE FLOW-ACCOMMODATING FLUID SHUNT

BACKGROUND OF THE INVENTION

This invention relates generally to surgically implantable physiological shunt systems and related flow control devices. More particularly, the present invention relates to shunt systems including one-way flow control devices for controlling the flow of cerebrospinal fluid out of a brain ventricle, and to capacitive elements in such shunt systems designed to reduce overdrainage of cerebrospinal fluid due to the pulsatile nature of cerebrospinal fluid flow.

In the medical arts, to relieve undesirable accumulation of fluids it is frequently necessary to provide a means for draining a fluid from one part of the human body to another in a controlled manner. This is required, for example, in the treatment of hydrocephalus, an ailment usually afflicting infants or children in which fluids accumulate within the skull and exert extreme pressure and skull deforming forces.

In treating hydrocephalus, cerebrospinal fluid accumulated in the brain ventricles is typically drained away utilizing a drainage or shunt system including a catheter inserted into the ventricle through the skull, which is connected to a tube which conducts the fluid away from the brain to be reintroduced into the peritoneal cavity or into the vascular system, as by extending a distal catheter through the patient's jugular vein to the atrium portion of the heart. To control the flow of cerebrospinal fluid and maintain the proper pressure in the brain ventricle, a pump or valve is placed in the conduit between the brain and the peritoneal cavity or the heart. An exemplary flow control device is found in U.S. Pat. No. 4,560,375.

Although such drainage systems have provided successful results, a problem of overdrainage of the cerebrospinal fluid from the brain ventricles sometimes exists. Overdrainage of cerebrospinal fluid may result in excessive reduction of the cerebrospinal fluid pressure within the brain ventricles and predispose the development of a subdural hematoma or hydroma, and excessive reduction of ventricular size leading to shunt obstruction because of impingement of the ventricular walls on the inlet holes of the ventricular catheter. This overdrainage can be caused by the siphoning effect of hydrostatic pressure in the distal shunt catheter. The siphoning effect of hydrostatic pressure may be created by the elevation of the ventricular catheter inlet with respect to the distal catheter outlet (i.e., when the patient sits, stands or is held erect). In order to prevent such overdrainage caused by the siphoning effect of hydrostatic pressure in the distal shunt catheter, siphon control devices have been placed in the conduit, typically between the flow control device and the peritoneal cavity or the heart. An exemplary siphon control device is found in U.S. Pat. No. 4,795,437.

Current cerebrospinal fluid shunts include flow control devices which are unidirectional by design. This characteristic is desirable to prevent reflux of distal fluids into the ventricular system. However, in normal physiology, as demonstrated by continuous magnetic residence imagery (MRI), cerebrospinal fluid flows in a pulsatile nature out of and back into the cerebellar structures as driven by increases and decreases in blood pressure. This pulsatile flow is compromised with the introduction of a one-way valve in the treatment of obstructive hydrocephalus.

Present flow control devices, by their nature, rectify the pulsatile normal flow (analogous to alternating current flow) of the cerebrospinal fluid into an abnormal uni-directional flow (analogous to electrical direct current flow). This can cause an increase in flow rate (overdrainage) due to the continuous expulsion of cerebrospinal fluid out of the ventricular system without allowing the natural return. Proximally induced overdrainage of cerebrospinal fluid often requires revision due to obstructed ventricular catheters.

Accordingly, there has been a need for a surgically implantable shunt system capable of reducing overdrainage of cerebrospinal fluid due to the pulsatile nature of cerebrospinal fluid flow. In this regard, a capacitive element is needed which allows for the placement of a uni-directional valve in the shunt system to prevent reflux while accommodating proximal pulsatile flow within the ventricular system. Additionally, such a novel capacitive element is needed which may be utilized in connection with existing cerebrospinal fluid flow control devices. The present invention fulfills these needs and provides other related advantages.

SUMMARY OF THE INVENTION

The present invention resides in a surgically implantable shunt system comprising means for restricting the flow of cerebrospinal fluid through the shunt, and means for accommodating the pulsatile nature of cerebrospinal fluid flow between a cerebrospinal fluid source and the flow restricting means. The flow restricting means normally prevents the flow of cerebrospinal fluid through the shunt system until fluid on an inlet side of the flow restricting means reaches a predetermined pressure, at which pressure cerebrospinal fluid is then permitted to flow through the flow restricting means in one direction. The accommodating means serves to reduce cerebrospinal fluid pressure fluctuations on the inlet side of the flow restricting means to reduce the incidence of proximally induced overdrainage of cerebrospinal fluid from the brain ventricles.

In a preferred form of the invention, the shunt system includes a fluid conduit having an inlet and an outlet, and a flow control device forming a portion of the fluid conduit between the fluid conduit inlet and the fluid conduit outlet. The flow control device includes the flow restricting means. A capacitive element is also provided which forms a portion of the fluid conduit between the fluid conduit inlet and the flow control device.

The capacitive element includes a reservoir having an inlet in fluid communication with the fluid conduit inlet, and an outlet in fluid communication with an inlet for the flow control device. Means are provided for accommodating the pulsatile fluid flow within the shunt between the fluid conduit inlet and the flow control device, by varying the fluid capacity of the reservoir in a manner reducing overdrainage of fluid through the shunt.

The reservoir includes a base defining the reservoir inlet and the reservoir outlet, and a housing for the base which, in connection with the base, defines a fluid flow pathway between the reservoir inlet and the reservoir outlet. The accommodating means includes a pair of spaced, substantially parallel, flexible diaphragms forming opposite sides of the housing, such that each flexible diaphragm has an outer surface which forms an exterior surface of the reservoir, and an inner surface in contact with and subject to pressure variations of fluid within the reservoir. Means are provided for shielding the flexible diaphragms from the influence of tissue surrounding the reservoir. The shielding means includes a raised ring surrounding each diaphragm and forming a recess in which the respective diaphragm is positioned.

The diaphragms form flexible membranes in direct communication with a reference atmospheric pressure on the outside of the capacitive element. The membranes are allowed to flex outwardly to increase the capacity of the reservoir during the systolic beat of the heart. During the diastolic fall in blood pressure, the ventricular system is free to retrieve a small amount of cerebrospinal fluid contained within the reservoir, and thus the pulsatile nature of cerebrospinal fluid flow is accommodated. The described process is repeated with each heartbeat. This reduces cerebrospinal fluid pressure fluctuations on the inlet side of the flow restricting means, which pressure fluctuations, during the systolic beat of the heart, have been known to cause fluid flow through the flow control device prematurely.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 4 is an enlarged sectional view of the capacitive element similar to that shown in FIG. 2, illustrating reflexation of a pair of diaphragms to increase the capacity of a fluid reservoir during the systolic beat of the heart; and FIG. 5 is a sectional view of the capacitive element similar to that shown in FIG. 4, illustrating contracture of the flexible diaphragms during the diastolic beat of the heart, wherein the capacity of the capacitive element is decreased.

DETAILED DESCRIPTION OF THE PREFERRED EMBODIMENT

Figure 1:
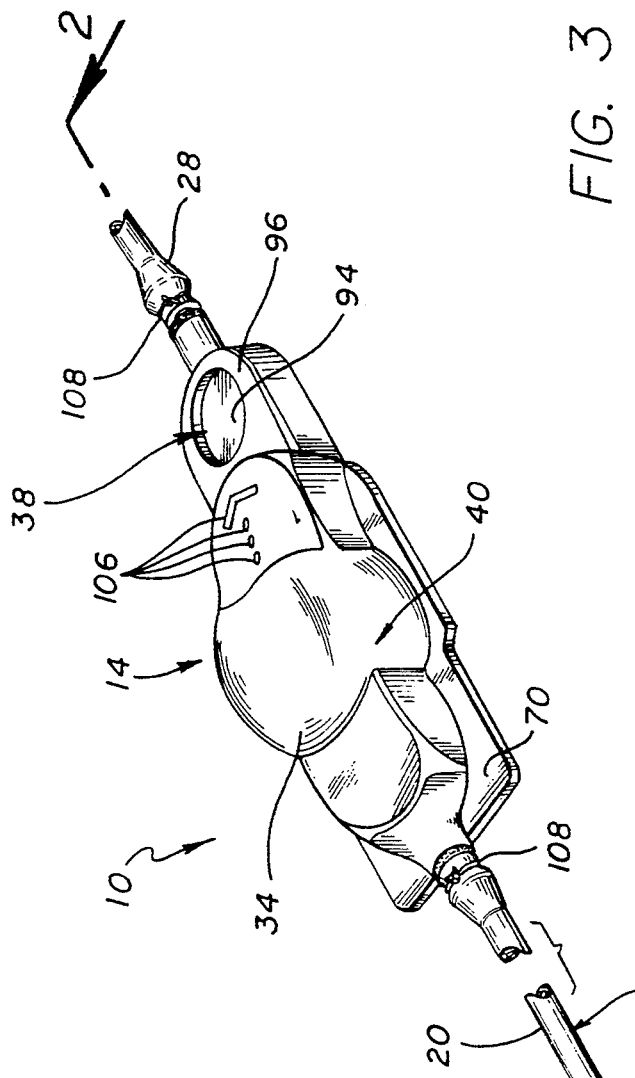
FIG. 1 is a partially fragmented perspective view of a pulsatile flow-accommodating cerebrospinal fluid shunt embodying the invention, and specifically showing a fluid conduit including a fluid flow control device and a capacitive element.
Figure 3:
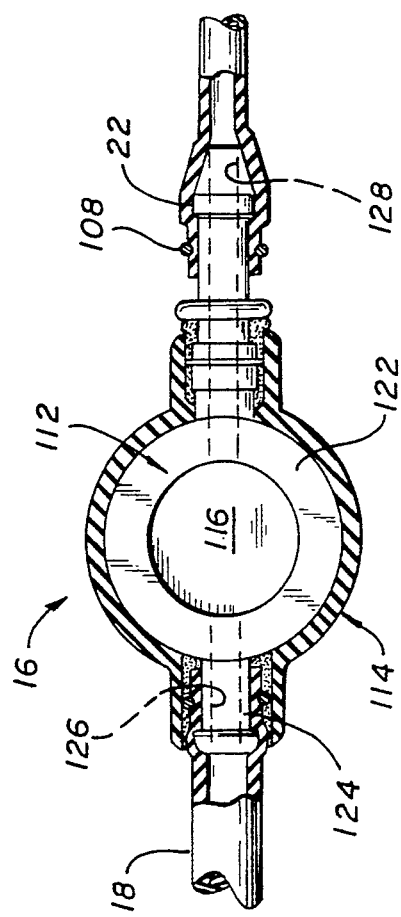
FIG. 3 is a fragmented, partially sectional view of the capacitive element taken generally along the line 3—3 of FIG. 2.

As shown in the drawings for purposes of illustration, the present invention is concerned with a surgically implantable shunt system, generally designated in the accompanying drawings by the reference number 10. The shunt system 10 comprises, generally, a fluid conduit 12 having an inlet and an outlet, a flow control device 14 forming a portion of the fluid conduit between the fluid conduit inlet and the fluid conduit outlet, and a capacitive element 16 which forms a portion of the fluid conduit between the fluid conduit inlet and the flow control device 14. When the shunt system 10 is intended for the treatment of hydrocephalus, the capacitive element 16 is connected with a proximal catheter 18 which is inserted through the skull into a brain ventricle containing cerebrospinal fluid under pressure. An intermediate section of surgical tubing 20 extends between and fluidly couples an outlet connector 22 of the capacitive element 16 and an inlet connector 24 of the flow control device 14. An outlet connector 26 of the flow control device 14 is fluidly connected to a distal catheter 28 which serves to discharge cerebrospinal fluid into, for example, the atrium portion of a patient's heart. Ordinarily the flow control device 14 and the capacitive element 16 will be surgically implanted on the patient's skull with a flap of skin overlying these portions of the shunt system 10.

The present invention is concerned primarily with the addition of the capacitive element 16 to the shunt system 10 which, when utilized in a cerebrospinal shunt, is utilized to reduce overdrainage of cerebrospinal fluid due to the pulsatile nature of cerebrospinal fluid flow. Before discussing the construction and operation of the capacitive element 16 in detail, however, the flow control device 14 will first be described to facilitate a better understanding of the implantable shunt system 10 in its entirety. In this regard, the flow control device 14 described below is shown and described in greater detail in U.S. Pat. No. 5,176,627, the contents of which are incorporated herein.

The flow control device 14 includes a pair of relatively rigid, molded plastic bases 30 and 32 invested within a resiliently flexible housing 34 which, together, define a fluid flow path through the housing from the inlet connector 24 to the outlet connector 26. A normally closed valve 36 is provided within the fluid flow path to restrict the flow of fluid through the device 14. The housing 34 and the second base 32 cooperate to provide a siphon control device 38 situated between the valve 36 and the outlet connector 26, which prevents fluid flow through the device 14 in the absence of positive upstream fluid pressure or in response to negative downstream hydrostatic pressure on the device. Further, the housing 34 and the first base 30 cooperate to define a pump or flushing reservoir 40 between the inlet connector 22 and the valve 36.

Figure 2:
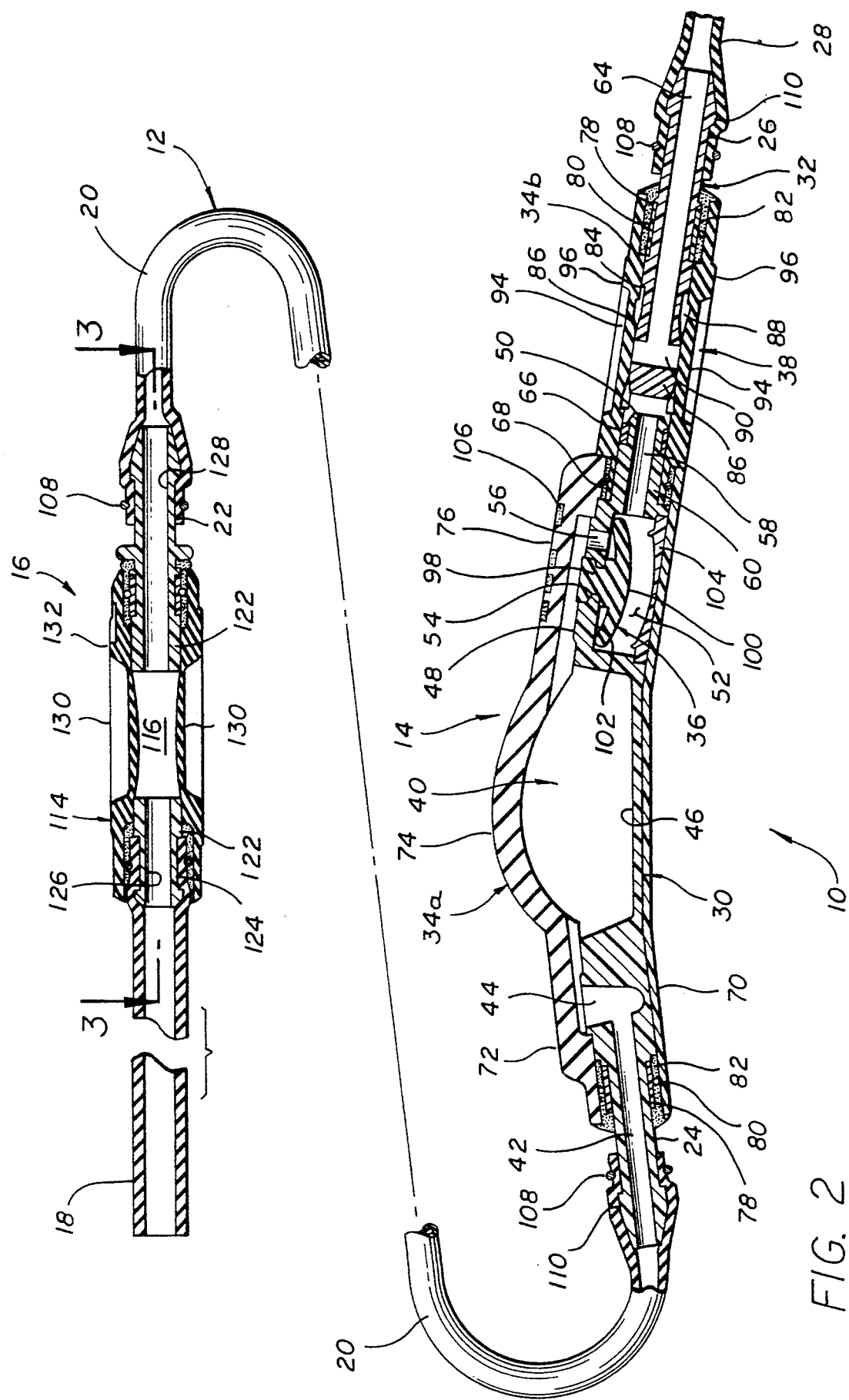
FIG. 2 is an enlarged, fragmented and partially sectional view taken generally along the line 2—2 of FIG. 1, illustrating the details of the capacitive element and the flow control device.

As shown best in FIG. 2, the bases 30 and 32 interfit with one another and are integrally formed with, respectively, the inlet and outlet connectors 24 and 26. The first or proximal base 30 is integrally formed with the inlet connector 24 and defines an inlet flow channel 42 extending through the inlet connector 24 to an upwardly facing inlet occluder port 44. The first base forms a bottom plate 46 for the flushing reservoir 40, a support 48 for the valve 36, and a snap-fit interlocking barbed connector 50.

The support 48 defines an outlet chamber 52 for the first base 30 into which the valve 36 extends. The support 48 includes a centrally positioned valve-supporting aperture 54, and three surrounding apertures 56 which permit fluid flow from an upper surface of the support 48 into the outlet chamber 52. An intermediate flow channel 58 extends from the outlet chamber 52 through the connector 50 to direct fluids from the first base 30 to the second base 32.

The barbed connector 50 extends from the base generally opposite to the inlet connector 24, and is supported by a housing support member 60. A pair of splines (not shown) extend from the housing support member 60 generally parallel to the longitudinal axis of the connector 50 and the intermediate flow channel 58.

The connector 50 and the splines interact with corresponding portions of the second base 32 to prevent tensile and torsional movement of the proximal and distal bases 30 and 32 with respect to one another.

In this regard, the second or distal base 32 is integrally formed with the outlet connector 26 which defines an outlet flow channel 64 therethrough. The second or distal base 32 defines a portion of the siphon control device 38. A connector receptacle 66 is provided in the proximal end of the second base 32 for receiving the barbed connector 50 therein. Spline receiving slots (not shown) are also provided in the proximal end of the second base, to slidably receive and substantially envelope the splines as the connector 50 is inserted into the receptacle 66.

The flexible housing 34 is provided in two parts: a first or inlet housing body 34a into which the first base 30 is invested, and an outlet or second housing body 34b which is sealed by a suitable adhesive 68 to the inlet housing body 34a in order to provide a continuous elastomeric exterior to the device 14, with the exception of the inlet and outlet connectors 24 and 26 which extend therefrom. The inlet housing body 34a is integrally formed with a mounting pad 70 and includes an inlet aperture through which the inlet connector 24 extends, an inlet occluder wing 72 which generally overlies the inlet occluder port 44, a resiliently flexible dome 74 for the flushing reservoir 40, and a distal occluder wing 76 generally overlying the support 48.

In order to provide a fluid-tight seal between the inlet connector 24 and the housing 34a, a tube 78 is placed over a portion of the inlet connector and secured in place by means of an over-suture 80. A silicone adhesive 82 is then injected into the remaining gap between the housing 34a and the inlet connector 24. This same sealing arrangement is utilized between the housing 34b and the outlet connector 26.

The inlet occluder wing 72 is positioned over the inlet occluder port 44 to facilitate occluding the inlet flow channel 42 at the port 44 by pressing the wing 72 downwardly. Depressing the wing 72 and occluding the port 44 prevents proximal fluid flow from the flushing reservoir 40, defined by the dome 74 and the bottom plate 46, when the dome is pressed downwardly by manual percutaneous pressure. The dome 74 is preferably molded of a silicone elastomer material and is designed to permit injection into the flow control device 14 by a hypodermic needle through the dome. The bases 30 and 32 are preferably molded of a polypropylene material which provides sufficient rigidity to prevent a needle from inadvertently passing through the device 14 if an injection is made into the flushing reservoir 40. The construction of the bases 30 and 32 and the housing 34 helps to guide a physician in manually percutaneously manipulating the device 20 when subcutaneously implanted, for purposes of flushing the shunt system.

The distal occluder wing 76 is positioned over the support 48 for the valve 36 to facilitate occluding the apertures 56. This is accomplished by pressing the wing 76 downwardly, which effectively prevents distal fluid flow from the flushing reservoir 40 when the dome is pressed downwardly by manual percutaneous pressure.

The outlet housing body 34b surrounds a portion of the second base 32 to define the siphon control device 38 which is similar to that shown and described in U.S. Pat. No. 4,795,437, the contents of which are incorporated herein by reference. The siphon control device 38 includes an outer wall 84 and an inner wall 86 which is situated within and encircled about by the outer wall. The intermediate flow channel 58 directs fluid from the outlet chamber 52 to a central SCD reservoir 88 defined as the area between the inner wall 86 and the outer wall 84. The outlet flow channel 64 extends through the inner wall 86 to the distal end of the outlet connector 26.

The outer wall 84 is generally circular in shape, and is spaced from and encircles the inner wall 86. The inner wall is also generally circular in shape, and defines an SCD outlet chamber 90 which is adjacent to and in fluid communication with the outlet flow channel 64. The inner wall 86 is constructed to have substantially parallel upper and lower seating surfaces 92, and it effectively forms a barrier separating the SCD reservoir 88 from the SCD outlet chamber 90.

The outlet housing body 34b is provided with a pair of spaced, substantially parallel, flexible elastic diaphragms 94 which are fixed about their peripheries adjacent to the outer wall 84. Each diaphragm has an inner surface which defines the upper and lower limits of the SCD reservoir 88 and the SCD outlet chamber 90, and an outer surface which forms an exterior surface of the siphon control device 38. The diaphragms 94 are situated on opposite sides of the inner wall 86 to position a portion of each inner surface thereof in contact with an adjacent one of the seating surfaces 92 and form a seal therebetween which prevents fluid flow between the outlet chamber 52 and the outlet flow channel 64.

The second housing body 34b further includes integral offset rings 96 which surround each diaphragm 94 to inhibit overlying tissue from occluding the siphon control device 38 when implanted into a patient. An aperture is provided through the housing 34b through which the outlet connector 26 extends. A fluid tight seal is effected between the housing outlet aperture and the outlet connector 26 utilizing a tube 78, an over-suture 80 and an adhesive 82, as described above in connection with the inlet housing body 34a and the inlet connector 24.

In use, the diaphragms 94 normally lie against and interact with the seating surfaces 92 of the inner wall 86 to close the device 14 to fluid flow. The diaphragms 94 move away from the seating surfaces 92, however, in response to a minimal level of positive fluid pressure within the SCD reservoir 88 to permit passage of fluid from the intermediate flow channel 58 to the outlet flow channel 64. The diaphragms 94 close and seal upon the seating surfaces 92 once again in the absence of such positive upstream fluid pressure, or in response to negative downstream hydrostatic pressure in the SCD outlet chamber 90. The siphon control device 38 thus minimizes the undesirable consequences attendant to excessive overdrainage of fluid due to the siphoning effect of hydrostatic pressure.

The normally closed valve 36 extends from the support 48 into the outlet chamber 52 for controlling the flow of cerebrospinal fluid out of a brain ventricle. The normally closed valve 36 includes a central support 98 and a resilient membrane 100 molded of a synthetic polymer material different from the material of the first base 30. The resilient membrane 100 is normally biased to close communication between the flushing reservoir 40 and the outlet chamber 52, but will open to permit flow through the apertures 56 when the pressure on the inlet or proximal side of the resilient membrane exceeds the pressure on the outlet or distal side by a predetermined amount. Moreover, should the pressure on the distal side of the resilient membrane 100 ever exceed the pressure on the proximal side, tending to cause flow in a reverse direction through the normally closed valve 36, the membrane 100 will seal tightly against a valve seat 102 provided on the support 48, to prevent any such reverse fluid flow.

The first base 30 is preferably formed of a polypropylene material, and the membrane 100 is preferably formed of a silicone elastomer material. Both polypropylene and elastomer materials have been shown to produce an acceptable level of tissue reaction, and the use of this particular duality of materials, in contrast to the use of only a single material, markedly decreases the chance of the membrane 100 adhering to any portion of the valve seat 102 which would clog the fluid pathway through the device 14 and defeat the purpose of the device.

The membrane 100 has an arch-shape, as for example a section of a sphere, and is designed to contact the valve seat 102 generally along the outer edges of the membrane in a manner surrounding the apertures 56. The membrane 100 is secured in place adjacent to the valve seat 102 by the central support 98 which is fixed within the valve aperture 54. A needle guard disc 104 is adhesively secured in place opposite the support 48, to generally enclose the outlet chamber 52.

Since the normally closed valve 36 is primarily designed to provide controlled resistance to cerebrospinal fluid flow from a brain ventricle to another location in the body, it will be appreciated that a doctor must be able to select a valve having the particular pressure/flow characteristics desired for each individual application. That is, a valve which permits flow at a relatively low pressure differential may not be suitable where the maintenance of a higher pressure differential is indicated. Toward this end, in order to provide a variety of valves having different pressure/flow characteristics, the valve 36 can be provided with a thick membrane 100 or a relatively thin membrane. Resistance to flow increases with the increase in membrane thickness.

The design of the flow control device 14 described above lends itself to easy percutaneous distal and proximal flushing. In order to flush the device 14 distally, the inlet occluder wing 72 is pressed downwardly to occlude the inlet occluder port 44. The dome 74 is then simply pressed downwardly to flush the contents of the flushing reservoir 40 past the normally closed valve 36, through the intermediate flow channel 58, then past the siphon control device 38 and through the outlet flow channel 64. Similarly, proximal flushing can be accomplished by pressing downwardly on the distal occluder wing 76 to occlude the apertures 56 through the support 48. The dome 74 is then pressed downwardly to flush fluid proximally from the flushing reservoir 40 out of the device 20 through the inlet flow channel 42.

If desired, radiopaque indicators 106 can be embedded into the upper surface of the housing 34.

In order to connect the distal catheter 28 to the outlet connector 26 of the flow control device 14, and to connect the intermediate surgical tubing 20 to the outlet connector 22 of the capacitive element 16 and to the inlet connector 24 of the flow control device 14, the respective ends of the catheter 28 and the surgical tubing 20 are placed over the respective connectors 22, 24 and 26 and secured thereon by a single ligature 108 just inside of an annular ridge 110 formed near the end of each connector.

In accordance with the present invention, the capacitive element 16 includes a generally cylindrical molded plastic base 112 which is invested within a flexible housing 114, which, together, define a fluid reservoir 116 within the capacitive element 16. The fluid capacity of the reservoir 116 is designed to increase during distal flow of cerebrospinal fluid indicated by the arrow 118 in FIG. 4 during the systolic beat of the heart, and diminish as the ventricular system retrieves a small amount of cerebrospinal fluid (as shown by the arrow 120 in FIG. 5) during the diastolic fall in blood pressure. Thus, the capacitive element 16 of the shunt system 10 provides means for accommodating the pulsatile nature of the cerebrospinal fluid flow between the cerebrospinal fluid source and the flow control device 14, and for reducing cerebrospinal fluid pressure fluctuations on the proximal side of the resilient membrane 100.

The base 112 includes a cylindrical outer wall 122, an inlet connector 124 and the outlet connector 22. An inlet flow channel 126 directs fluid received from the proximal catheter 18 through the inlet connector 124 and the outer wall 122 into the fluid reservoir 116. An outlet flow channel 128 directs fluid from the fluid reservoir 116 through the outer wall 122 and the outlet connector 22 to the intermediate section of surgical tubing 20.

In order to provide a fluid-tight seal between the inlet connector 124 and the housing 114, the distal end of the proximal catheter 18 is placed over the connector 124 and secured thereon by a single ligature 108.

The housing 114 is provided with a spaced, substantially parallel, flexible elastic diaphragms 130 which are fixed about their peripheries adjacent to the outer wall 122. Each diaphragm 130 has an inner surface which defines the upper and lower limits of the fluid reservoir 116, and an outer surface which forms an exterior surface of the capacitive element 16. The housing 114 further includes integral raised rings 132 which surround each diaphragm 130 to help shield the flexible diaphragms from the influence of tissue overlying the capacitive element 16 when implanted in a patient. The raised rings 132 form recesses in which the diaphragms 130 are positioned.

Apertures are provided through the housing 114 through which the inlet connector 124 and the outlet connector 22 of the base 112 extend. A fluid tight seal is effected between the housing outlet aperture and the outlet connector 22 utilizing a tube 134, an over-suture 136 and an adhesive 138, as described above in connection with the inlet housing body 34a and the inlet connector 24 of the flow control device 14. The adhesive 138 is also applied between the distal end of the proximal catheter 18 and the housing inlet aperture in the same manner.

In use, the diaphragms 130 flex outwardly as shown in FIG. 4 during the systolic beat of the heart to increase the capacity of the fluid reservoir 116 as a small amount of cerebrospinal fluid is pumped into the system but prevented from passing entirely therethrough by the flow control device 14. During the diastolic fall in blood pressure, the variable capacity fluid reservoir 116 permits a small amount of cerebrospinal fluid to be retrieved by the ventricular system, during which time the restoration force of the elastomeric diaphragms 130 causes a reduction in the overall fluid capacity of the fluid reservoir 116. This process is repeated with each heartbeat to accommodate the pulsatile nature of cerebrospinal fluid flow and reduce cerebrospinal fluid pressure fluctuations on the proximal side of the resilient membrane 100.

From the foregoing it is to be appreciated that the present invention provides a novel implantable shunt system 10 which utilizes a capacitive element 16 to reduce overdrainage of the shunted fluid due to the effects of cyclicly rising and falling blood pressure on the shunted fluid. The capacitive element 16 in a cerebrospinal fluid shunt is provided between the proximal catheter 18 and the flow control device 14 to temporarily store excess cerebrospinal fluid pumped into the shunt system 10 during the systolic beat of the heart, for retrieval during the immediately subsequent diastolic fall in blood pressure.

Although a particular embodiment of the invention has been described in detail for purposes of illustration, various modifications may be made without departing from the spirit and scope of the invention. Accordingly, the invention is not to be limited except as by the appended claims.

I claim:

1. A capacitive element in a physiologic fluid shunt, for reducing overdrainage of fluid due to the pulsatile nature of fluid flow, the capacitive element comprising:
   a reservoir having an inlet in fluid communication with a cerebrospinal fluid source, and an outlet in fluid communication with means for restricting the flow of fluid through the shunt; and
   means for accommodating the pulsatile nature of fluid flow between the fluid source and the flow restricting means by varying the fluid capacity of the reservoir, the accommodating means including a flexible diaphragm having an outer surface which forms an exterior surface of the reservoir, and an inner surface in contact with and subject to pressure variations of fluid within the reservoir.

2. A capacitive element as set forth in claim 1, including means for shielding the flexible diaphragm from the influence of tissue surrounding the reservoir.

3. A capacitive element as set forth in claim 2, wherein the shielding means includes a raised ring surrounding the diaphragm and forming a recess in which the diaphragm is positioned.

4. A capacitive element as set forth in claim 1, wherein the reservoir includes a base defining the inlet and the outlet, and a housing for the base which, in connection with the base, defines a fluid flow pathway between the inlet and the outlet.

5. A capacitive element as set forth in claim 4, wherein the accommodating means includes a pair of spaced, substantially parallel, flexible diaphragms forming opposite sides of the housing, wherein each flexible diaphragm has an outer surface which forms an exterior surface of the reservoir, and an inner surface in contact with and subject to pressure variations of fluid within the reservoir.

6. A capacitive element as set forth in claim 5, including means for shielding the flexible diaphragms from the influence of tissue surrounding the reservoir, wherein the shielding means includes a raised ring surrounding each diaphragm and forming a recess in which the respective diaphragm is positioned.

7. A capacitive element as set forth in claim 1, wherein the flow restricting means normally prevents the flow of fluid therethrough until fluid on an inlet side of the flow restricting means reaches a predetermined pressure, at which pressure fluid is then permitted to flow through the restricting means in one direction.

8. A cerebrospinal fluid shunt, comprising:
   means for restricting the flow of cerebrospinal fluid through the shunt, wherein the flow restricting means normally prevents the flow of cerebrospinal fluid therethrough until the cerebrospinal fluid on an inlet side of the flow restricting means reaches a predetermined pressure, at which pressure cerebrospinal fluid is then permitted to flow through the flow restricting means in one direction; and
   means for accommodating the pulsatile nature of cerebrospinal fluid flow between a cerebrospinal fluid source and the flow restricting means, and for reducing cerebrospinal fluid pressure fluctuations on the inlet side of the flow restricting means, the accommodating means including a reservoir having an inlet in fluid communication with the cerebrospinal fluid source and an outlet in fluid communication with the flow restricting means, and a flexible diaphragm having an outer surface which forms an exterior surface of the reservoir and an inner surface in contact with and subject to pressure variations of cerebrospinal fluid within the reservoir, wherein the flexible diaphragm permits the fluid capacity of the reservoir to be variable.

9. A cerebrospinal fluid shunt as set forth in claim 8, wherein the reservoir includes a base defining the inlet and the outlet, and a housing for the base which, in connection with the base, defines a fluid flow pathway between the inlet and the outlet.

10. A cerebrospinal fluid shunt as set forth in claim 8, including means for shielding the flexible diaphragm from the influence of tissue surrounding the reservoir.

11. A cerebrospinal fluid shunt as set forth in claim 10, wherein the shielding means includes a raised ring surrounding the diaphragm and forming a recess in which the diaphragm is positioned.

12. A cerebrospinal fluid shunt as set forth in claim 8, wherein the flow restricting means includes a flow control valve and a siphon control device.

13. A surgically implantable shunt system, comprising:
   a fluid conduit having an inlet and an outlet;
   a flow control device forming a portion of the fluid conduit between the fluid conduit inlet and the fluid conduit outlet, the flow control device providing means for restricting the flow of fluid through the shunt, wherein the flow restricting means normally prevents the flow of fluid therethrough until fluid on an inlet side of the flow control device reaches a predetermined pressure, at which pressure fluid is then permitted to flow through the flow control device in one direction; and
   a capacitive element forming a portion of the fluid conduit between the fluid conduit inlet and the flow control device, the capacitive element including a reservoir having an inlet in fluid communication with the fluid conduit inlet, an outlet in fluid communication with an inlet for the flow control device, a base defining the reservoir inlet and the reservoir outlet, and a housing for the base which, in connection with the base, defines a fluid flow pathway between the reservoir inlet and the reservoir outlet, and means for accommodating pulsatile fluid flow within the shunt between the fluid conduit inlet and the flow control device by varying the fluid capacity of the reservoir in a manner reducing overdrainage of fluid through the shunt, the accommodating means including a pair of spaced, substantially parallel, flexible diaphragms forming opposite sides of the housing, such that each flexible diaphragm has an outer surface which forms an exterior surface of the reservoir, and an inner surface in contact with and subject to pressure variations of fluid within the reservoir.

14. A surgically implantable shunt system as set forth in claim 13, including means for shielding the flexible diaphragms from the influence of tissue surrounding the reservoir, wherein the shielding means includes a raised ring surrounding each diaphragm and forming a recess in which the respective diaphragm is positioned.

15. A surgically implantable shunt system as set forth in claim 14, wherein the flow control device includes a uni-directional flow control valve and a siphon control device.

* * * * *